United States Patent [19]

Farquhar

[11] Patent Number: 5,091,552
[45] Date of Patent: * Feb. 25, 1992

[54] NOVEL ANTITUMOR ALDOPHOSPHAMIDE ANALOGS

[75] Inventor: David Farquhar, Houston, Tex.

[73] Assignee: Board of Regents, The University of Texas System, Austin, Tex.

[*] Notice: The portion of the term of this patent subsequent to Jun. 20, 2006 has been disclaimed.

[21] Appl. No.: 323,423

[22] Filed: Mar. 14, 1989

Related U.S. Application Data

[63] Continuation-in-part of Ser. No. 879,910, Jun. 30, 1986, Pat. No. 4,841,085.

[51] Int. Cl.$^5$ .................. C07F 1/30; C07F 9/36; C07H 15/252; C07H 17/02
[52] U.S. Cl. .................. 558/180; 536/6.4; 536/29; 558/199; 558/200; 562/10
[58] Field of Search .................. 558/180

[56] References Cited

U.S. PATENT DOCUMENTS 4,841,085  6/1989  Farquhar et al. .................. 538/180
4,841,910  6/1989  Farquhar .................. 558/180

FOREIGN PATENT DOCUMENTS 0098601  1/1984  European Pat. Off. .
2429795  1/1980  France .

OTHER PUBLICATIONS

Filoslav Beran, Borje S. Andersson, Yugiang Wang, Kenneth B. McCredie, and David Farquhar: Cancer research 48, 339–345, Jan. 15, 1988. The Effects of Acetaldophosphamide, a Novel Stable Aldophosphamide Analogue, n Normal Human and Leukemic Progenitor Cells in Vitro: Implications for Use in Bone Marrow Purging.
A. Takamizawa et al.: Journal of the American Chemical Society, vol. 95, No. 3, Feb. 7, 1973. "Studies on Cyclophosphamide metabolites and their related compounds. II. Preparation of an active species."
Sladek (1973), Cancer Res., 33:1150.
Conners, et al. (1974), Biochemical Pharmacol., 23:115.
Cox, et al. (1975), Cancer Res., 35:3755.
Friedman, et al. (1979), Adv. Cancer Chemother., 1:143.
Sharkis, et al. (1980), Blood, 55:521.
Korbling, et al. (1982), Brit. J. Haematol., 52:89.
Hilton, et al. (1984), Proc. Amer. Assoc. Cancer Res.
Hilton, (1984), Biochem. Pharmacol., 33:1867.
Hilton, (1984), Cancer Res., 44:5156.
Sladek, et al. (1985), Cancer Res., 45:1549.
Stewart, et al. (1985), Exp. Hematol, 13:267.
Struck, et al. (1975), Heyden and Son, Ltd.
Norpoth, (1976), Cancer Treatment Reports, 60:437.
Peter, et al. (1976), Cancer Treatment Reports, 60:429.
Struck, (1976), Cancer Treatment Reports, 60:317.
Frei, et al. (1977), Cancer Treatment Reports, 61:1209.
Farquhar, et al. (1979), J. of Labelled Compounds and Radiopharmaceuticals, XVI:615.
Farquhar, et al. (1980), J. Labelled Compounds and Radiopharmaceuticals, XVII:159.
Zon, et al. (1982), J. Pharm. Sci., 71:443.
Farquhar, et al. (1983), J. Med. Chem., 26:1153.
Farquhar, et al. (1983), J. Pharmaceutical Sciences, 72:324.
Garattini, (1983), European J. of Drug Metabolism and Pharmacokinetics, 8:97.
Struck, et al., (1983), Brit. J. Cancer, 47:015–026.
Herve', (1984), Investigational New Drugs, 2:245.
Struck et al, (1984), Cancer Treatment Reports, 68:765.
de Jong, et al., (1985), Cancer Res., 45:4001.
Gordon, et al. (1985), Leukemia Research, 9:1017.
Kohn et al., (1985), Biochem. Pharmacol., 34:3465.
Smith et al., (1985), Biochem. Pharmacol., 34:3459.
Yeager, et al., Jul. 17, 1986, The New England Journal of Medicine, vol. 315.
Kohn, (1987), Cancer Res. 47:3180.
Montgomery et al, (1976), Cancer Treatment Rep., 60:381.
Struck, (1974), Cancer Res., 34:2933.

*Primary Examiner*—Mukund J. Shah
*Assistant Examiner*—E. Bernhardt
*Attorney, Agent, or Firm*—Arnold, White, and Durkee

[57] ABSTRACT

A compound having the structure:

(Abstract continued on next page.)

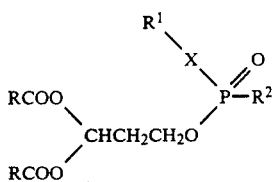

wherein R is $CH_3$, $C_2H_5$, $C_3H_7$, t—$C_4H_9$ or $C_6H_5$; $R^1$ is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OC_2C_6H_5$, $CH_3$, $C_2H_5$, $C_3H_7$, $C_4H_9$, $CH_2NO_2$ or $CH_2NH_2$; and $R^2$ is $NHCH_2CH_2Cl$ or $N(CH_2CH_2Cl)_2$.

These compounds may be used to eliminate occult leukemic clonogenic cells from bone marrow by contacting the bone marrow with a solution comprising levels of said compound sufficient to eliminate occult leukemic clonogenic cells. Analogously, tumor cells in a host or organ of a host may be eliminated by treatment of the host or host's organ with a compound of this description.

Compounds of this description are stable aldophosphamide analogs activatable by the action of an esterase and a subsequent E-2 elimination reaction to form acrolein and a phosphoramidic mustard of the formula:

A stable aldophosphamide analog activatable by the action of an esterase and a subsequent spontaneous E-2 elimination reaction to form acrolein and a phosphoramidic mustard, said phosphoramidic mustard having the formula

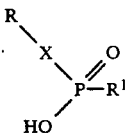

R is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7(_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OC_2C_6H_5$, $CH_3$, $C_2H_5$, $C_3H_7$, $C_4H_9$, $CH_2NO_2$ or $CH_2NH_2$; and $R^1$ is $NHCH_2CH_2Cl$ or $N(CH_2CH_2Cl)_2$.

1 Claim, 7 Drawing Sheets

COMPOUND 20-E : R = CH₃,
COMPOUND 21-E : R = CH₂CH₃

WITH DOXORUBICIN, X - OH

WITH DAUNOMYCIN, X - H

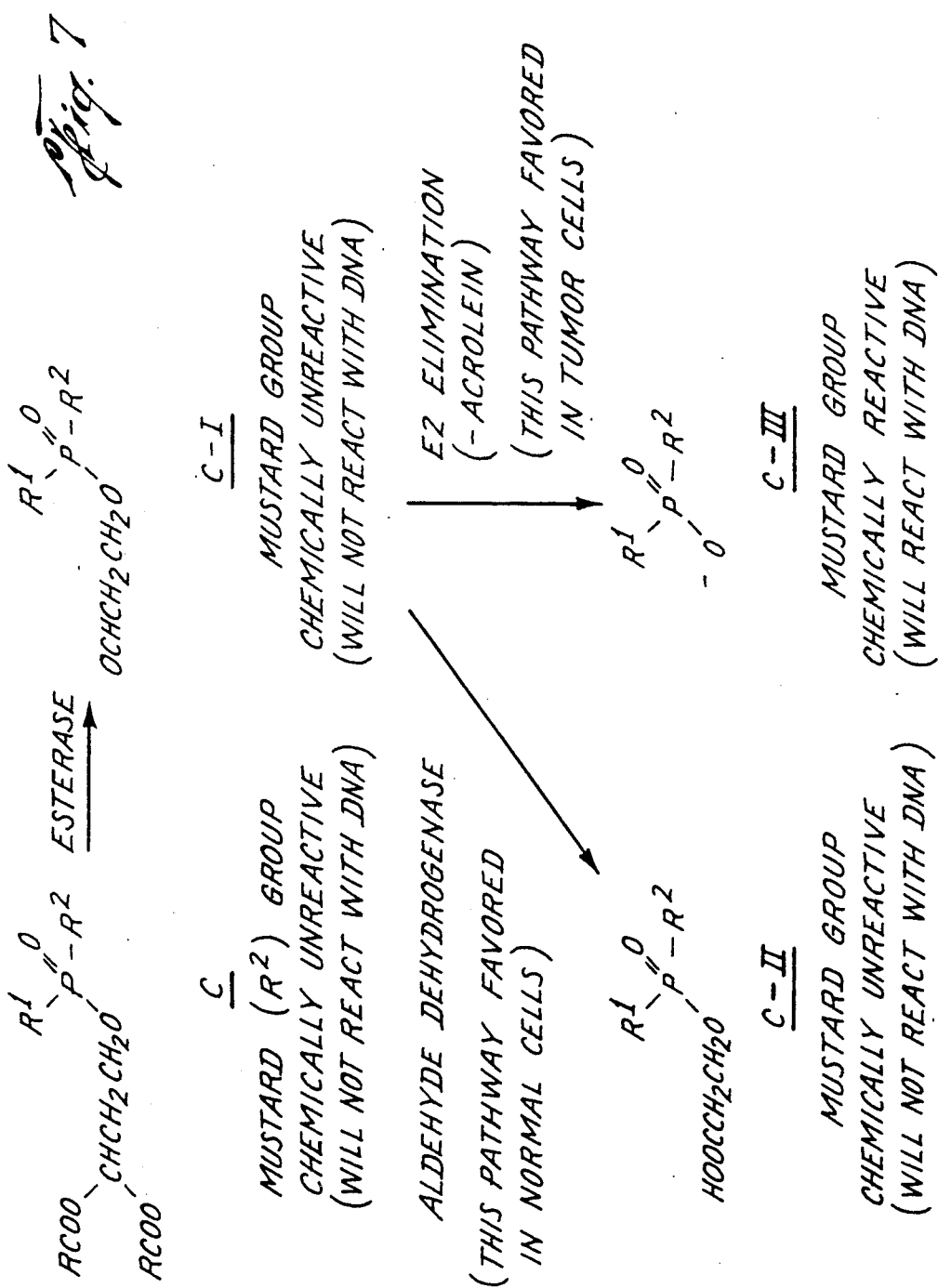

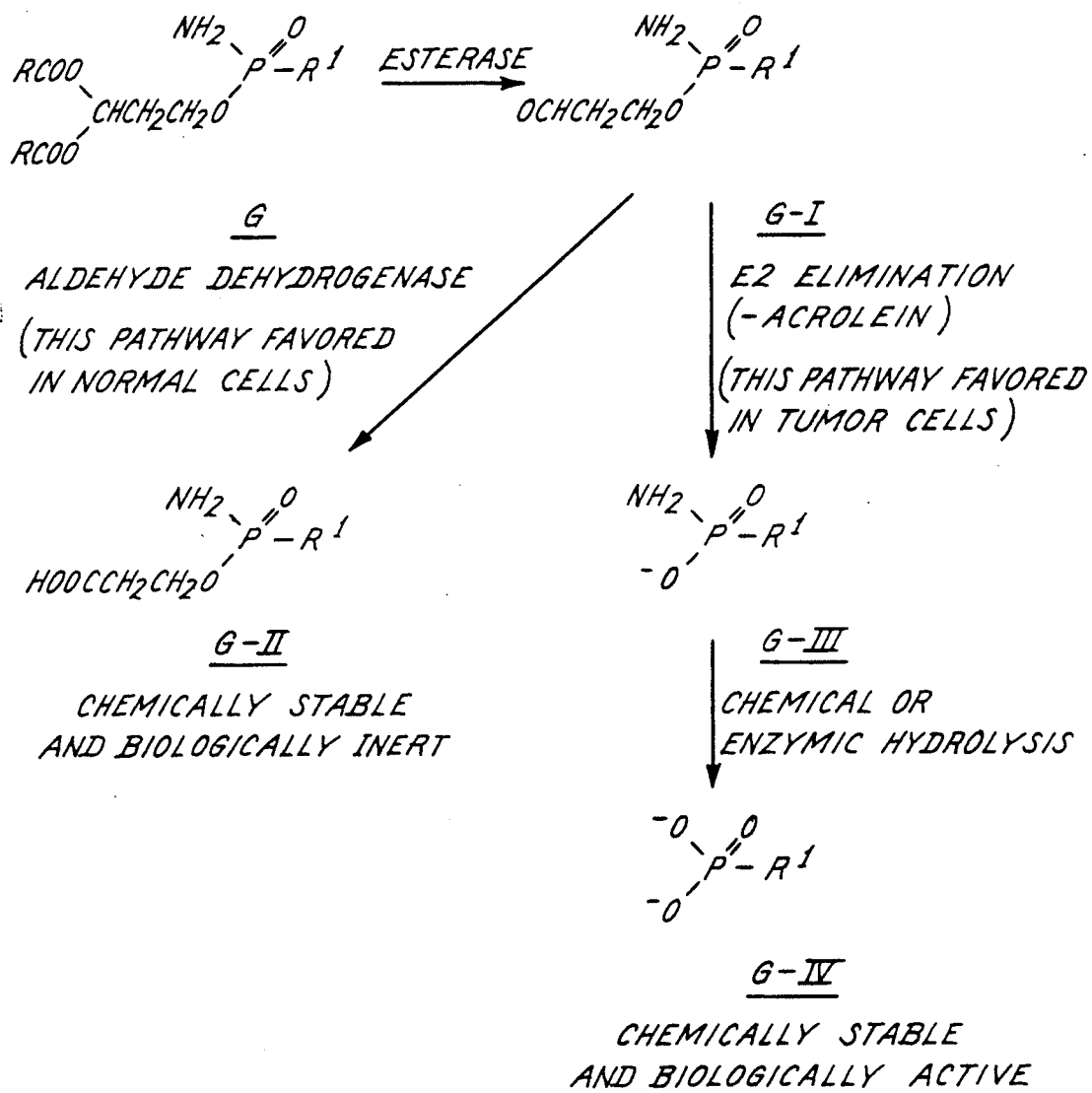

NOVEL ANTITUMOR ALDOPHOSPHAMIDE ANALOGS

This is a continuation-in-part of application Ser. No. 06/879,910 filed June 30, 1986 now issued as U.S. Pat. No. 4,841,085, June 20, 1989.

BACKGROUND OF THE INVENTION

The present intention relates to cyclophosphamide analogs particularly useful for the suppression of tumor cells.

Since the demonstration in 1942 that nitrogen mustard was effective at inducing remissions in patients with lymphoma (A. Gilman Amer. J. Surg. 105:574), several thousand structural analogs have been synthesized in an attempt to enhance the selectivity of the parent drug. However, only a few of these compounds have demonstrated sufficient therapeutic superiority to nitrogen mustard in experimental tumor systems to warrant clinical trial. Of these, cyclophosphamide is unquestionably the most important. It has a higher therapeutic index than must other mustard-type alkylating agents and a much broader spectrum of clinical activity. However, the drug is not independently cytotoxic; it requires enzymatic activation in order to exert biologic activity. Although the biotransformation of cyclophosphamide, in vivo, is complex, the following general principles (FIG. 1) are widely accepted (D. L. Hill (1975) A Review of Cyclophosphamide' (Charles C. Thomas, Springfield, Ill. and O. M. Friedman, et al. (1979) Adv. Cancer Chemother. 1:143).

As shown in FIG. 1, Cyclophosphamide, (1-A), is oxidatively biotransformed, mainly in the liver, by cytochrome P-450 dependent mixed-function oxidases to give 4-hydroxycyclophosphamide, (2-A). This metabolite exists in equilibrium with aldophosphamide (3-A), its open-chain tautomer. Aldophosphamide is labile and undergoes an E2 elimination reaction to generate phosphorodiamidic mustard (5-A) and acrolein (6-A). 4-Hydroxycyclophosphamide and aldophosphamide also undergo further enzymatic oxidation, the former mediated by alcohol dehydrogenases and the latter by aldehyde dehydrogenases or aldehyde oxidases, to give, respectively, 4-ketocyclophosphamide (4-A) and carboxyphosphamide (7-A). Compounds 4-A and 7-A are chemically stable and relatively non-toxic. Phosphorodiamidic mustard (5), a potent alkylating agent, is generally considered to be the ultimate 'active metabolite' of cyclophosphamide.

Although widespread agreement exists on the metabolism of cyclophosphamide, its mechanism of antitumor selectivity has been controversial. However, strong evidence has recently been presented in favor of the Selective Detoxification Hypothesis. The key feature of this hypothesis, first proposed by Sladek ((1973) Cancer Res. 33:1150), and later by Connors, et al. ((1974) Biochemical Pharmacol. 23:114), and Cox, et al. ((1975) Cancer Res. 35:3755), is that the conversion of aldophosphamide to carboxyphosphamide, a biologically inert compound, is less efficient in tumor cells than in most drug-susceptible normal cells (e.g., hematopoietic stem cells) because the latter contain higher levels of aldehyde dehydrogenases. As a consequence, more aldophosphamide dissociates to the highly cytotoxic phosphorodiamidic mustard in tumor cells. It has now been demonstrated that intracellular levels of aldehyde dehydrogenases are, indeed, an important biologically-operative determinant of the antitumor selectivity of cyclophosphamide. Thus, Hilton and Colvin have shown (J. Hilton, et al. (1984) Proc. Amer. Assoc. Cancer Res. 25:339) that intracellular levels of aldehyde dehydrogenase correlate inversely with cyclophosphamide sensitivity both in a variety of human and rodent hematopoietic cell lines, and in human leukemic cells; high aldehyde dehydrogenase levels were present in drug-resistant cells. An L1210 resistant cell-line with unusually high aldehyde dehydrogenase activity was rendered drug-sensitive (J. Hilton (1984) Biochem. Pharmacol. 33:1867) by pretreating the cells with low concentrations of disulfiram, an aldehyde dehydrogenase inhibitor. Equally significant, 4-hydroxycyclophosphamide was extensively converted to carboxyphosphamide, an inactive metabolite, when incubated with extracts from the drug resistant L1210 cell-line (J. Hilton (1984) Cancer Res. 44:5156). By contrast, negligible levels of carboxyphosphamide, were formed when 4-hydroxycyclophosphamide was incubated, under the same conditions, with extracts from the drug-sensitive cell line. The author concluded (J. Hilton (1984) Cancer Res. 4:5156): '4-Hydroxycyclophosphamide and/or aldophosphamide is the form in which cyclophosphamide reaches these tumor cells in mice and that intracellular aldehyde dehydrogenase activity is an important determinant of cyclophosphamide sensitivity in these cell lines'.

Sladek has reported (N. E. Sladek, et al. (1985) Cancer Res. 45:1549) that three known (and one suspected) inhibitors of aldehyde dehydrogenase activity [disulfiram, diethyl dithiocarbamate, cyanamide, and (ethylphenyl (2-formylethyl) phosphinate)] potentiate the cytotoxicity of 4-hydroperoxycyclophosphamide and ASTA Z 7557 (Conference proceedings published in: (1984) Investigational New Drugs 2:1–259), (both latent precursors of 4-hydroxycyclophosphamide) when incubated against cyclophosphamide-resistant L1210 and P-388 cell-lines. Significantly, no potentiation was observed with phosphordiamidic mustard, the presumed active metabolite of cyclophosphamide. In further studies, Sladek has shown (F. R. Kohn, et al. (1984) Proc. Amer. Assoc. Cancer Res. 25:289); (F. R. Kohn, et al. (In press) Biochem. Pharmacol) that aldehyde dehydrogenase activity is an important determinant of the differential sensitivities of murine pluripotent hematopoietic stem cells and granulocytemacrophage myeloid pregenitor cells to various activated cyclophosphamide analogs, including 4-hydroperoxycyclophosphamide and ASTA Z 7557. This finding likely accounts for the relative sparing effect of cyclophosphamide on myeloid stem cells.

Friedman, et al. (O. M. Friedman (1979) Adv. Cancer Chemother. 1:143) and, more recently, Zon (G. Zon (1982) Progress in Medicinal Chemistry 19:205) have strongly emphasized the need for further investigations in the mechanism of selectivity of cyclophosphamide and its analogs. The present application relates to new information that is critically relevant to this question. An important advantage of the present invention is the incorporation of structural and mechanistic features that contribute to the selectivity of cyclophosphamide into other antitumor drugs to enhance their therapeutic efficacy.

Advances in the treatment of acute myeloid leukemia in adults has generally been due to the introduction of new cytostatic drugs. The most important of these have been arabinosyl cytosine (Ara-C), the anthracyclines, and m-AMSA. Different combinations of these drugs give remission rates of about 60-70% (R. P. Gale (1977) Lancet 1:497); (J. F. Holland, et al. (1976) Arch. Intern. Med. 136:1377); and (K. B. McCredie, et al. (1981) Proc. A.S.C.O. and AACR 22:479); however, the median duration of complete remission is less than 18 months, with a "cured" fraction of less than 20%.

In contrast, long-term release-free survival can be achieved in about 50% of AML-patients after high-dose chemotherapy and total body irradiation followed by allogeneic bone marrow transplantation in first remission (R. A. Clift, et al. (1985) Blood 66(5):887 (Abstract); (A. Fefer, et al. (1983) Blood 57:421); and, (K. G. Blume, et al. (1980) N. Engl. J. Med. 302:1041). Similar results have been obtained in patients with relapsing or refractory acute leukemia who receive bone marrow transplantation from an identical twin, after supralethal chemoradiotherapy (R. L. Powles, et al. (1980) Lancet 1:1047). Unfortunately, only about 25% of all patients have an HLA-compatible sibling available or bone marrow donation. The patient's own bone marrow can, however, be harvested in complete remission, cryopreserved, and used as a source of syngeneic hematopoietic stem cells for graftment purpose. This procedure allows a transplantation conditioning regimen with high-dose chemo- or chemoradiotherapy aimed at eradicating dormant leukemic cells in sanctuary sites like testicles, ovaries and the central nervous system. The problem that prevents more widespread use of cryopreserved autologous bone marrow is the presence of occult clonogeneic leukemic cells in remission bone marrow. Thus, results obtained with autologous bone marrow transplantation for AML in first remission do not differ significantly from that obtained with chemotherapy alone (A. Fefer, et al. (1983) Blood 57:421). Ten evaluable patients were treated in second remission, with high-dose chemotherapy followed by autologous marrow transplant. Of those, one was alive in remission at 30 months, seven relapsed (range 1-8 months) and two died early. The feasibility of using in vitro immunologic or pharmacologic treatment of remission bone marrow to eliminate occult leukemic clonogeneic cells capable of causing relapse of the disease has been convincingly proven in animal model systems (P. Stewart, et al. (1985) Exp. Hematol. 13:267); (S. J. Sharkis, et al. (1980) Blood 55:521); (H. Coizer, et al. (1982) proc AACR 23:194); (M. Korbling, et al. (1982) Br. J. Haematol 52:89); and, (S. Thierfelder, et al. (1977) Eur J. Cancer 15:1357). Early data for in vitro treatment ("purging") of human remission bone marrow indicate that methodology can be designed that allows successful engraftment of the patients with in vitro manipulated marrow. The available methods that have been used so far include:

(a) treatment of bone marrow with antibodies plus complement;
(b) treatment with antibodies linked to a toxin e.g. ricin;
(c) pharmacologic treatment with an in vitro active drug.

The major weakness with the immunological "purging" methods is the lack of proven specific acute leukemia antigens that would distinguish leukemic cells from normal hemopoietic stem cells. Another technical problem is the limited availability of large quantities of monoclonal antibodies for in vitro treatment of large volumes of bone marrow.

For pharmacologic purging, the ideal drug(s) should preferably selectively kill leukemic stem cells while leaving the normal stem cells intact to allow for hemopoietic reconstitution. Obviously, such techniques alleviate the problem of finding specific anti-leukemia antibodies. Another advantage is that drug can easily be manufactured in large quantities under standardized conditions. One drug that has a possible selective action against leukemic versus normal cells is cyclophosphamide Its in vitro active congener 4-hydroperoxycyclophosphamide, has recently received much attention for purging purposes both in murine models (P. Stewart, et al. (1985) Exp. Hematol. 13:267); (S. J. Sharkis, et al. (1980) Blood 55:521); (H. Coizer, et al. (1982) Proc AACR 23:194); (M. Korbling, et al. (1982) Br. J. Haematol. 52:89); (S. Thierfelder, et al. (1977) Eur. J. Cancer 15:1357); (E. S. Vitetta, et al. (1982) Immunol. Rev. 62:160) and in a clinical setting (A. Hagenbeck and A. C. M. Martens (1981) Exp. Hematol. 10 (Suppl. 11):14); (H. Kaizer, et al. (1981) Exp. Hematol. 9 (Suppl. 372):190) and, (L. Douay, et al. (1982) Exp. Hematol. 10 (Suppl. 12):113.

The major shortcomings of 4-hydroperoxycyclophosphamide (4-HC) is that it has a relatively short half-life in vitro (less than 2 hrs) and that its toxic action decreases with increasing cell concentration. Furthermore, the supply of doses is limited. To circumvent these short-comings, a new series of in vitro active oxazaphosphorines is a subject of the present invention. The present application relates to investigating the in vitro activity of these compounds in human myeloid leukemic cell lines that have been developed and recently characterized, both the parent lines and sublines resistant to two of the other major anti-leukemic drugs, adriamycin and m-AMSA in comparison to their action on normal committed myeloid stem cells and pluripotent hemopoietic stem cells. A long-term goal of the present invention enables the techniques that may be applied in clinical setting for autologous bone marrow transplantation.

Among the objectives of the present invention are:
(1) to develop a model for in vitro treatment of human bone marrow, obtained from patients with acute myeloid leukemia in complete remission, with a novel series of in vitro active oxazaphosphorines,
(2) to determine the optimal condition under which maximum leukemic clonogeneic cell kill can be achieved with sparing of hemopoietic regenerative capacity,
(3) to examine possible quantitative differences between myeloid leukemic and normal hemopoietic stem cells in the make-up of activating and degrading enzymatic machinery responsible for the resulting cytotoxicity, and
(4) to explore different avenues of manipulating cellular aldehydrogenase activity, thereby augmenting differences in cytotoxicity between normal and leukemic clonogeneic stem cells.

SUMMARY OF THE INVENTION

In one view, the present invention involves a compound having the structure:

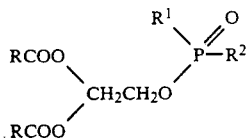

wherein R is $CH_3C_2H_5$, $C_3H_7$, $t-C_4H_9$ or $C_6H_5$; $R^1$ is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OCH_2C_6H_5$, $CH_3$, $C_2H_5$, $C_3H_7$, $C_4H_9$, $CH_2NO_2$ or $CH_2N_2$ and $R^2$ is $NHCH_2CH_2Cl$ or $N(CH_2CH_2Cl)_2$.

Any one of these compounds may be used to eliminate occult leukemic clonogenic cells from bone marrow by contacting the bone marrow with a solution comprising sufficient levels of said compound. Analogously, tumor cells in a host or organ of a host may be eliminated by treatment of the host or host's organ with a compound of this description.

Compounds of this description are stable aldophosphamide analogs activatable by the action of an esterose and a subsequent elimination reaction to form acrolein and a phosphoramidic mustard of the formula:

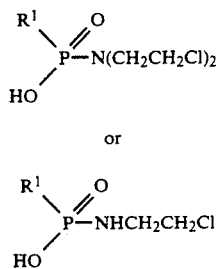

wherein $R^1$ is $NH_2$, $NHCH_3$, $NHC_2H_5$, $NCH_3H_7$, $NHC_4H_9$, $NHCH_2CH_2Cl$, $NHC_6H_5$, $N(CH_3)_2$, $NC(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OCH_2C_6H_5$, $CH_3$, $C_2H_5$, $C_3H_7$, $C_4H_9$, $CH_2NO_2$ or $CH_2NH_2$.

The present invention may be further described as including a compound having the structure

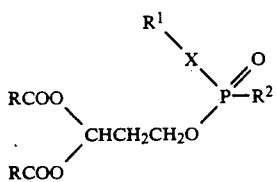

wherein:
R is alkyl, aryl, or alkaryl;
X is N, NH, NHNH, NHO, ONH, alkyl;
$R^1$ is hydrogen, alkyl, dialkyl, aryl, chloroalkyl, nitro, amine, benzyloxycarbonyl or t-butoxycarbonyl; and
$R^2$ is chloroethylamine or bis(chloroethyl)amine.

Additionally included in the present invention is a compound having the structure:

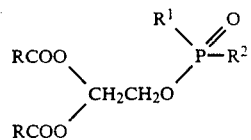

wherein:
R is $CH_3$, $C_2H_5$, $C_3H_7$, $t-C_4H_9$ or $C_6H_5$;
$R^1$ is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OC_2C_6H_5$, $CH_3$, $C_2H_5$, $C_3H_7$, $C_4H_9$, $CH_2NO_2$ or $CH_2NH_2$; and
$R^2$ is $NHCH_2CH_2Cl$ or $N(CH_2CH_2Cl)_2$.

In broader view, the present invention describes stable aldophosphamide analogs activatable by the action of an esterase and a subsequent spontaneous E-2 elimination reaction to form acrolein and a phosphoramidic mustard, said phosphoramidic mustard having the formula

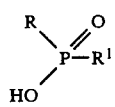

wherein:
R is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OC_2C_6H_5$, $CH_3$, $C_2H_5$, $C_3H_5$, $C_3H_7$, $C_4H_9$, $CH_2NO_2$ or $CH_2NH_2$; and
$R^1$ is $NHCH_2CH_2Cl$ or $N(CH_2CH_2Cl)_2$.

Additionally, the present invention involves a compound having the structure:

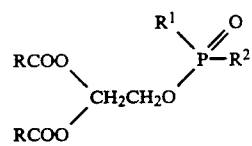

wherein:
R is $CH_3$, $C_2H_5$, $C_3H_7$, $C(CH_3)_3$ or $C_6H_5$;
$R^1$ is $NH_2$, $NHCH_3$, $NHCH_2CH_3$, $NHCH_2CH_2Cl$, $N(CH_3)_2$, $N(CH_2CH_3)_2$, $N(CH_2CH_2Cl)_2$, $NHCH_2CH_2CH_2CH_3$, $NCH_3(C_2H_5)$, $NCH_3(C_3H_7)$, $NHC_6H_5$, $NHOH$, $NHNHCO_2CH_2C_6H_5$, $NHNHCO_2C(CH_3)_3$, $OCH_3$, $OCH_2CH_3$, $OC_3H_7$, $OC_4H_9$, $OC_6H_5$, $OCH_2C_6H_5$, $ONHCO_2C(CH_3)_3$, $OCH_2CH_2CH(OAc)_2$, $OP(O)N(CH_2CH_2Cl)_2$, $CH_3$, $CH_2CH_3$, $CH_2CH_3$, $CH_2CH_2CH_3$, $CH_2CH_2CH_2CH_3$, $CH_2NO_2$, or $CH_2NH_2$; and
$R_2$ is $N(CH_2CH_2Cl)_2$ or $NHCH_2CH_2Cl$.

Compounds of the present invention include those having the structure:

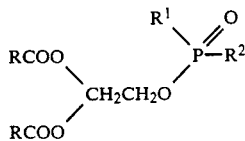

wherein: R is $CH_3$, $C_2H_5$, $C_3H_7$, $C(CH_3)_2$ or $C_6H_5$;
$R^1$ is a cytotoxic glycoside; and
$R^2$ is $N(CH_2CH_2Cl)_2$ or $NHCH_2CH_2Cl$.

In more particularity, the $R^1$ cytotoxic glycoside is N-(3')-Doxorubicin or N-(3')-Daunorubicin. Such adriamycin derivatives should be selectively activated in tumor cells and be effective chemotherapeutic agents.

Another chemotherapeutic compound of the present invention is one having the structure:

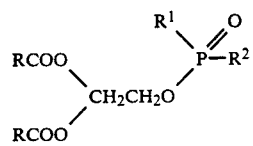

wherein:
R is $CH_3$, $C_2H_5$, $C_3H_7$, $C(CH_3)_2$ or $C_6H_5$;
$R^1$ is $NH_2$; and
$R^2$ is a nucleoside.
Preferred $R^2$ nucleosides are 2',3'-dideoxyuridine-5'yl and 5-methyl-2',3'- dideoxyuridine.

BRIEF DESCRIPTION OF THE DRAWINGS

FIG. 7 shows the proposed activation mechanism of compounds of the present invention.

FIG. 8 shows the anticipated mechanism of action of compounds of the present invention.

DESCRIPTION OF THE PREFERRED EMBODIMENTS

Figure 1:
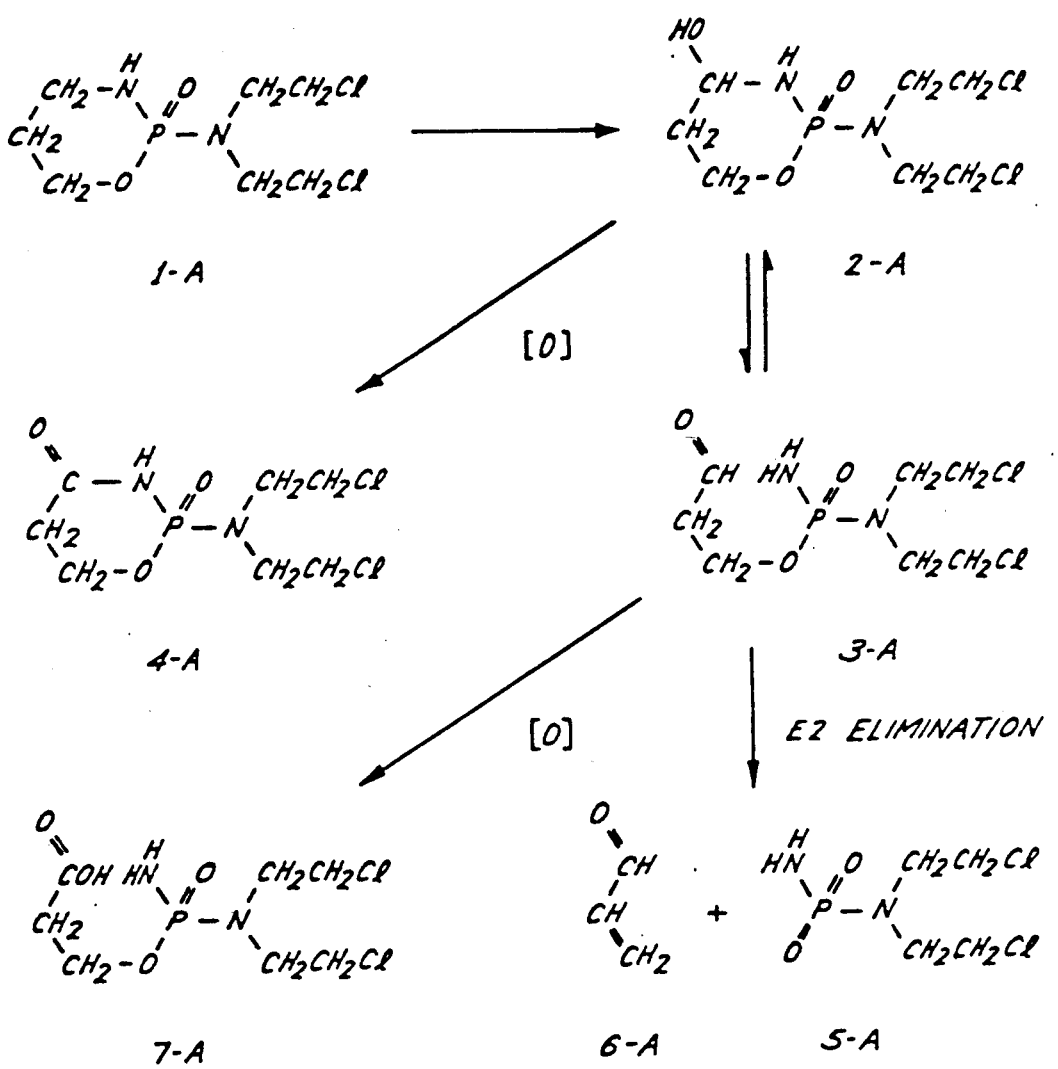
FIG. 1 schematically shows the generally accepted pathway for cyclophosphamide metabolism.

Objectives of this invention include the synthesis, biological evaluation and therapeutic use of a series of analogs of aldophosphamide, one of the major primary metabolites of cyclophosphamide. The analogs are designed to elucidate the structural correlates of antitumor activity for this general class of compounds, particularly the contribution of intermediate '4-hydroxy' cyclic structures to drug selectivity. A further major goal is to extend these key structural features to other cytotoxic agents in an attempt to enhance their therapeutic efficacy.

Novel aspects of studies with aldophosphamide analogs have shown that the analogs, unlike aldophosphamide, are chemically stable under neutral aqueous conditions. However, in the presence of carboxylate hydrolases (esterases), they will convert rapidly to unstable intermediates. Some of these intermediates can form cyclic derivatives, and exhibit chemical and biologic properties similar to those of aldophosphamide; other analogs which cannot cyclize, may exhibit substantially different properties. Correlation of the biologic properties of these compounds with their physicochemical characteristics should help clarify the structural correlates of antitumor selectivity.

Many compounds of the present invention are comprised in the following list. These new compounds have the following general structure:

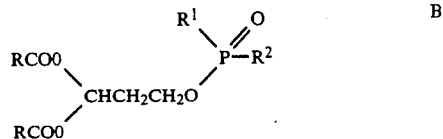

Where R, $R^1$ and $R^2$ are shown in Table 1 below for fifty-three model compounds.

TABLE 1

| Compound No. | R | $R^1$ | $R^2$ |
|---|---|---|---|
| B-1) | $CH_3$ | $NH_2$ | $N(CH_2CH_2Cl)_2$ |
| B-2) | $CH_3$ | $NHCH_3$ | $N(CH_2CH_2Cl)_2$ |
| B-3) | $CH_3$ | $NHCH_2CH_3$ | $N(CH_2CH_2Cl)_2$ |
| B-4) | $CH_3$ | $NHCH_2CH_2Cl$ | $N(CH_2CH_2Cl)_2$ |
| B-5) | $CH_3$ | $N(CH_3)_2$ | $N(CH_2CH_2Cl)_2$ |
| B-6) | $CH_3$ | $N(CH_2CH_3)_2$ | $N(CH_2CH_2Cl)_2$ |
| B-7) | $CH_3$ | $N(CH_2CH_2Cl)_2$ | $N(CH_2CH_2Cl)_2$ |
| B-8) | $CH_3$ | $OCH_3$ | $N(CH_2CH_2Cl)_2$ |
| B-9) | $CH_3$ | $OCH_2CH_3$ | $N(CH_2CH_2Cl)_2$ |
| B-10) | $CH_3$ | $CH_3$ | $N(CH_2CH_2Cl)_2$ |
| B-11) | $CH_3$ | $CH_2CH_3$ | $N(CH_2CH_2Cl)_2$ |
| B-12) | $CH_3$ | $NHCH_2CH_2Cl$ | $NHCH_2CH_2Cl$ |
| B-13) | $C_2H_5$ | $NH_2$ | $N(CH_2CH_2Cl)_2$ |
| B-14) | $C_2H_5$ | $NHCH_3$ | $N(CH_2CH_2Cl)_2$ |
| B-15) | $C_2H_5$ | $NHCH_2CH_2Cl$ | $NHCH_2CH_2Cl$ |
| B-16) | $C_2H_5$ | $NHCH_2CH_2Cl$ | $N(CH_2CH_2Cl)_2$ |
| B-17) | $C_2H_5$ | $N(CH_2CH_2Cl)_2$ | $N(CH_2CH_2Cl)_2$ |
| B-18 | $CH_3$ | $NHCH_2CH_2CH_3$ | $N(CH_2CH_2Cl)_2$ |
| B-19 | $CH_3$ | $NHCH_2CH_2CH_2CH_3$ | $N(CH_2CH_2Cl)_2$ |
| B-20 | $CH_3$ | $NCH_3(C_2H_5)$ | $N(CH_2CH_2Cl)_2$ |
| B-21 | $CH_3$ | $NCH_3(C_3H_7)$ | $N(CH_2CH_2Cl)_2$ |
| B-22 | $CH_3$ | $NHC_6H_5$ | $N(CH_2CH_2Cl)_2$ |
| B-23 | $CH_3$ | $NHOH$ | $N(CH_2CH_2Cl)_2$ |
| B-24 | $CH_3$ | $NHNHCO_2CH_2C_6H_5$ | $N(CH_2CH_2Cl)_2$ |
| B-25 | $CH_3$ | $NHNHCO_2C(CH_3)_3$ | $N(CH_2CH_2Cl)_2$ |
| B-26 | $CH_3$ | $OC_3H_7$ | $N(CH_2CH_2Cl)_2$ |
| B-27 | $CH_3$ | $OC_4H_9$ | $N(CH_2CH_2Cl)_2$ |
| B-28 | $CH_3$ | $OC_6H_5$ | $N(CH_2CH_2Cl)_2$ |
| B-29 | $CH_3$ | $OCH_2C_6H_5$ | $N(CH_2CH_2Cl)_2$ |
| B-30 | $CH_3$ | $ONHCO_2C(CH_3)_3$ | $N(CH_2CH_2Cl)_2$ |
| B-31 | $CH_3$ | $OCH_2CH_2CH(OAc)_2$ | $N(CH_2CH_2Cl)_2$ |
| B-32 | $CH_3$ | $OP(O)N(CH_2CH_2Cl)_2$ | $N(CH_2CH_2Cl)_2$ |
| B-33 | $CH_3$ | $CH_2CH_2CH_3$ | $N(CH_2CH_2Cl)_2$ |
| B-34 | $CH_3$ | $CH_2CH_2CH_2CH_3$ | $N(CH_2CH_2Cl)_2$ |
| B-35 | $CH_3$ | $CH_2NO_2$ | $N(CH_2CH_2Cl)_2$ |
| B-36 | $CH_3$ | $CH_2NH_2$ | $N(CH_2CH_2Cl)_2$ |
| B-37 | $CH_3$ | $CH_2CH_2CH_3$ | $N(CH_2CH_2Cl)_2$ |
| B-38 | $CH_3$ | $CH_2CH_2CH_2CH_3$ | $N(CH_2CH_2Cl)_2$ |
| B-39 | $C_3H_7$ | $NH_2$ | $N(CH_2CH_2Cl)_2$ |
| B-40 | $C_3H_7$ | $NHCH_3$ | $N(CH_2CH_2Cl)_2$ |
| B-41 | $C_3H_7$ | $NHCH_2CH_2Cl$ | $NHCH_2CH_2Cl$ |
| B-42 | $C_3H_7$ | $NHCH_2CH_2Cl$ | $N(CH_2CH_2Cl)_2$ |
| B-43 | $C_3H_7$ | $N(CH_2CH_2Cl)_2$ | $N(CH_2CH_2Cl)_2$ |
| B-44 | $C(CH_3)_3$ | $NH_2$ | $N(CH_2CH_2Cl)_2$ |
| B-45 | $C(CH_3)_3$ | $NHCH_3$ | $N(CH_2CH_2Cl)_2$ |
| B-46 | $C(CH_3)_3$ | $NHCH_2CH_2Cl$ | $NHCH_2CH_2Cl$ |
| B-47 | $C(CH_3)_3$ | $NHCH_2CH_2Cl$ | $N(CH_2CH_2Cl)_2$ |
| B-48 | $C(CH_3)_3$ | $N(CH_2CH_2Cl)_2$ | $N(CH_2CH_2Cl)_2$ |
| B-49 | $C_6H_5$ | $NH_2$ | $N(CH_2CH_2Cl)_2$ |
| B-50 | $C_6H_5$ | $NHCH_3$ | $N(CH_2CH_2Cl)_2$ |
| B-51 | $C_6H_5$ | $NHCH_2CH_2Cl$ | $NHCH_2CH_2Cl$ |
| B-52 | $C_6H_5$ | $NHCH_2CH_2Cl$ | $N(CH_2CH_2Cl)_2$ |

TABLE 1-continued

| Compound No. | R | R¹ | R² |
|---|---|---|---|
| B-53 | $C_6H_5$ | $N(CH_2CH_2Cl)_2$ | $N(CH_2CH_2Cl)_2$ |

Figure 2:
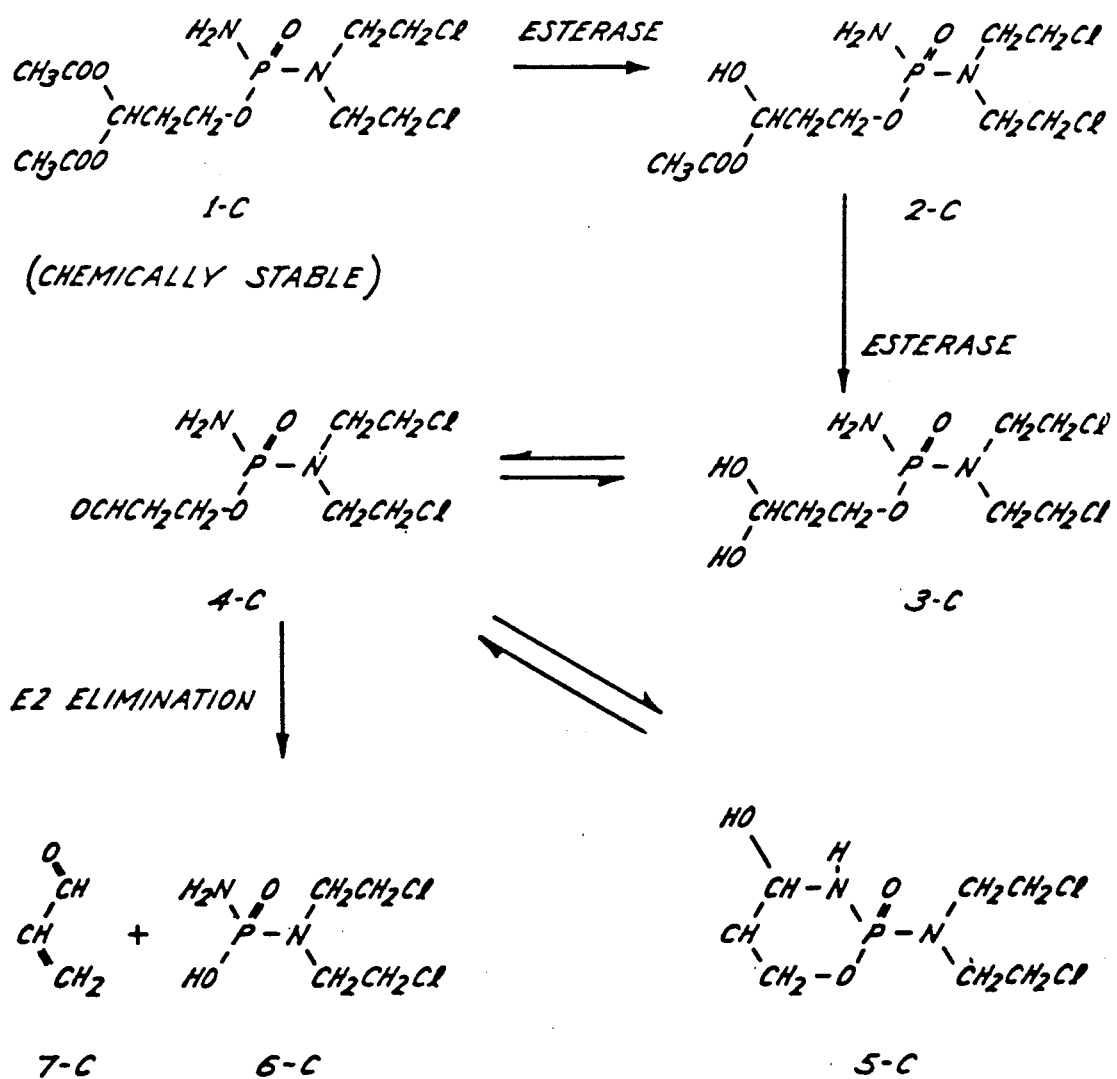
FIG. 2 schematically shows the activation pathway for compounds of the present invention.

The mechanism of activation of these compounds can be illustrated with respect to compound B-1. In the presence of carboxylate esterase, one of the carboxylate ester bonds of compound B-1 (1-C in FIG. 2) is cleaved (FIG. 2) to generate the corresponding hemiacetal, 2-C. This compound then undergoes cleavage of the second ester group to give the hydrate, 3-C, which exists in equilibrium with the free aldehyde, 4-C. The hemiacetal, 2-C, may also spontaneously eliminate acetic acid to give the aldehyde, 4-C, directly. Once generated, the aldehyde, 4-C, will rapidly tautomerize to form an equilibrium mixture with 4-hydroxycyclophosphamide, 5-C. However, since aldehyde, 4-C, is inherently chemically labile, the tautomeric mixture will gradually dissociate by an E2 elimination reaction to generate the potently cytotoxic phosphoramide mustard, 6-C, and acrolein, 7-C.

The biologic properties of the new latent aldophosphamides are dependent on the steric and electronic character of the R, R¹, and R² substituents, since these parameters influence (1) the rate at which the compounds are bioactivated (2) the position of equilibrium of the aldophosphamide/4-hydroxycyclophosphamide tautomeric mixtures (3) the susceptibilities of the aldophosphamides to E2 elimination and (4) the chemical reactivities of the ultimate alkylating phosphoramide mustards. An understanding of the contribution of these substituents to the antitumor and immunosuppressive properties of this novel class of compounds is vital to the application of the above concepts in the design of further new organophosphate therapeutic agents.

These new compounds have many potential application in medicine, particularly clinical oncology. One important application, autologous bone marrow transplantation, has already been mentioned. Another is the regional perfusion of tumors. Yet another is the local treatment of organ (e.g., pleural) tumor effusions. The new agents are also well suited to in vitro tumor sensitivity determination prior to systemic drug administration. However, long range goals relating to the present invention are to exploit the above concepts to develop new structural types of antitumor and immunosuppressive agents that exert their activities by molecular mechanisms fundamentally different from that of cyclophosphamide. The potential to develop such agents is now at hand.

The present invention comprises synthesis and uses of stable precursors of aldophosphamide that convert rapidly to the free aldehyde under physiologic conditions. Despite extensive endeavor, this has never been accomplished before. An excellent review of this entire area of investigation has been provided by Zon et al. (G. Zon (1982) Progress in Medicinal Chemistry 19:205). Currently, all preactivated analogs of cyclophosphamide that are used as experimental tools or that possess clinical promise (e.g. 4-hydroxycyclophosphamide, 4-hydroperoxycyclophosphamide, ASTA Z 7557), are cyclic structures that give rise to the ultimate active metabolites through the intermediacy of 4-hydroxycyclophosphamide. Major stability and formulation problems exist with many of these compounds. The opportunity to conduct mechanistic and therapeutic studies on analogs that initially give rise to aldophosphamide or to closely related structures, some of which cannot cyclize, has never before existed. Stable, open-chain aldophosphamide precursors that facilely generate the corresponding free aldehydes under physiologic conditions are inherently chemically and biologically interesting. Clearly, they are as useful, both as experimental tools and as clinical agents, as the ASTA series of compounds prepared in Germany that are the focus of intense experimental and clinical investigation and was the subject of a major international conference (Conference proceedings published (1984) Investigational New Drugs 2:1-259).

An unlimited number of stable, chemically-diverse, aldophosphamide analogs can readily be prepared using the approach described herein. Since the activating esterases are ubiquitous in tissue (K. Krisch (1971) The Enzymes 5:44, Academic Press), the compounds will facilely convert to the corresponding free aldehydes in all biological media, including tissue culture. The approach, therefore, is extremely broad in scope. By contrast, only a few 'preactivated' cyclic analogs are known. These latter compounds are synthesized from cyclophosphamide by a stepwise sequence in low overall yield. They are difficult to purify and are inherently chemically labile. Moreover, their limited availability and high cost are prohibitive of their widespread clinical use. It is not surprising that few such compounds have been reported, and that systemic structure/activity relationship studies with thee compounds have never been undertaken. In addition cellular pharmacology studies with cyclic preactivated analogs are exceedingly difficult because radiolabeled formulations are not readily accessible. By comparison, none of these problems exist with the aldophosphamide analogs of the present invention.

The requirement for cyclic structural geometry places severe constraints on the types of analogs that can be prepared, severely limiting structure activity studies. These considerations are far from academic because the mechanistic principles that contribute to the antitumor selectivity of cyclophosphamide should be extendable, in principle, to a wide variety of other structures but be unrealizable, in practice, because of the severe molecular constraints imposed by the ring configuration. Using the new approach of the present invention, virtually any conceivable analog of the general formulae, C, described below, can now be readily prepared (for structure-activity relationship studies, if necessary) with the important added assurance that it will almost certainly be activated in vivo. This approach cannot even be considered using cyclic structures.

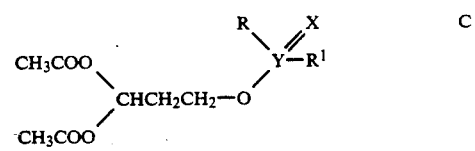

Wherein Y is P or S; X is O, S or NZ (Z is H or alkyl); one or both of R and R¹ is (are) cytotoxins (when only one is a cytotoxin, the other is H, $CH_2Z$, $NZ_2$,) OZ or SZ (where Z is H or alkyl)). Typical cytotoxins include adriamycin, nucleoside derivatives and phosphoramidic mustards.

One major application of the strategy, and one that constitutes an important object of the invention described herein, is to extend the above principles to antitumor nucleosides in order to enhance their therapeutic efficacy.

A series of cyclophosphamide analogs has been synthesized and evaluated to elucidate their mechanism of oncostatic selectivity for cancer cells. The $ED_{50}$ values of these compounds against L1210 lymphatic leukemia cells have been determined. Some of these analogs have been found to have a greater therapeutic efficancy than ASTA Z 7557 with an in vitro assay.

Cyclophosphamide(1-A) shown in FIG. 1, is a widely used antitumor drug. Its metabolism has been well known (FIG. 1). It is first activated in liver by "mixed-function" oxidases to give the intermediate 4-hydroxycyclophosphamide(2-A), which undergoes a rapidly equilibrium with its open-chain tautomer aldophosphamide(3-A). The aldophosphamide degrades spontaneously to give 3-carbon-unit acrolein(4-A) and the ultimate cytotoxic moiety, phosphoramide mustard(5-A). During the biotransformation process. Some other reactions also occur. 4-Hydroxycyclophosphamide is reduced by dehydrogenases to give 4-ketocyclophosphamide(6-A), which is biologically inactive. Aldophosphamide is reduced by either aldehyde dehydrogenases or aldehyde oxidases or both to give carboxyphosphamide(7-A), which is non-toxic.

Although this pathway of cyclophosphamide metabolism has been generally accepted, less is known with certainty about the mechanisms of the cytotoxic selectivity of the cyclophosphamide. It has been proposed, as mentioned earlier herein, that the conversion of aldophosphamide to carboxyphosphamide, a biologically inactive metabolite, is less efficient in tumor cells than in normal cells because the tumor cells contain less aldehyde dehydrogenases than the normal cells. As a consequence, more of the highly cytotoxic phosphoramide mustard, which is considered to be the 'ultimate active metabolite', is formed from the aldophosphamide in the tumor cells.

The present invention concerns a series of compounds which are chemically stable, but are converted to aldehyde compounds rapidly in the presence of carboxylate esterases. Some of these compounds can cyclize but some cannot.

Certain compounds of the present invention may be expressed as having the structure

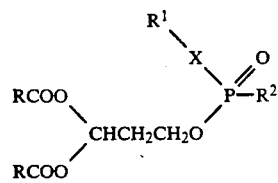

wherein R is alkyl, aryl, or alkaryl; X is N, NH, NHNH, NHO, ONH, or alkyl; $R^1$ is hydrogen, alkyl, dialkyl, aryl, chloroalkyl, nitro, amino, benzyloxycarbonyl or t-butoxycarbonyl; $R^2$ is chloroethylamine or bis(chloroethyl)amine.

Occult leukemic clonogenic cells may be eliminated from bone marrow by contacting the bone marrow with a solution comprising a sufficient level of one or more of the above compounds. Tumor cells from a host or an organ of a host may be likewise eliminated. A sufficient level of one or more of the above compounds is generally between about 5 mg/ml and about 30 mg/ml.

The compounds of the present invention represent new and effective tools for selectively eliminating occult leukemic clonogenic cells from bone marrow.

The following examples are presented to describe preferred embodiments and utilities of the present invention and are not meant to limit the present invention unless otherwise stated in the claims appended hereto.

EXAMPLE 1

SYNTHESIS OF CYCLOPHOSPHAMIDE ANALOGS

Figure 3:
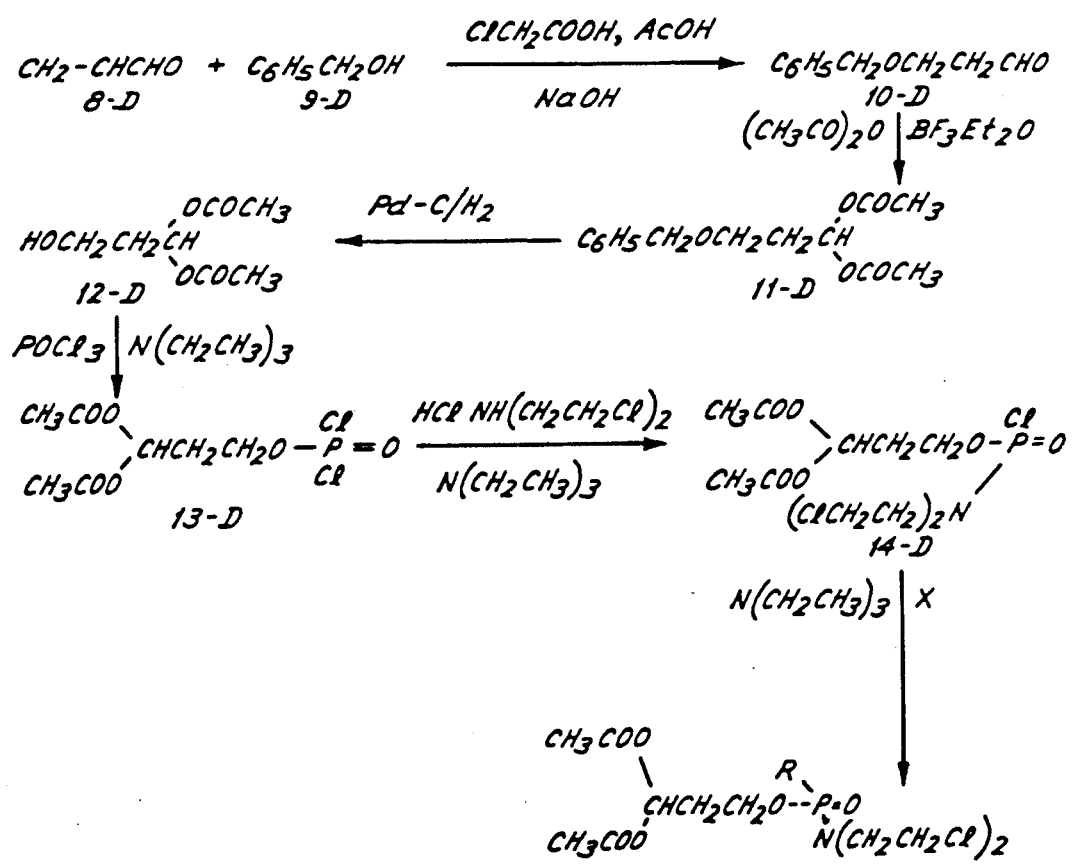
FIG. 3 schematically shows a synthetic pathway for compounds of the present invention.

The synthetic pathways are shown in FIG. 3. Acrolein, 8-D, was reacted with benzyl alcohol, 9-D, in the presence of monochloroacetic acid, acetic acid and sodium hydroxide as a catalyst, to give compound 10-D (Yamaguchi, et al. (1971) Chem. Abs. 74:523). Compound 10-D and acetic anhydride reacted rapidly to give compound 11-D in the presence of boron trifluoride/diethyl etherate (Edmund L. Niedzielski (1966) Chem. Abs. 65:6980). Compound 11-D was hydrogenolized over palladium-on-charcoal to give compound 12-D, which was crystallized with cooling. 1 equivalent of compound 12-D and triethylamine were added to 3 equivalents of phosphorus oxychloride (Takamizawa, et al., J. Med. Chem. 18 4.376) then 1 equivalent of bis(2-chloroethyl)amine hydrochloride and triethylamine were added. When the reaction was completed, the reaction mixture was washed with water and phosphate buffer, subjected to column chromatography, and eluted with ethylacetate and hexane. Compound 14-D was obtained as an oil. The amine [$NH_3$, HCl $NH_2CH_3$, HCl $NH_2CH_2CH_3$, HCl $N(CH_3)_2$, or $NH(CH_2CH_3)_2$] was reacted with 14-D to give compound 15-D, 16-D, 17-D, 18-D or 19-D respectively (FIG. 3).

The acrolein (99%), benzyl alcohol (99%), acetic anhydride (A.C.S. reagent), phosphorous oxychloride (99%), bis(2-chloroethyl)amine hydrochloride (98%), ethylamine (anhydrous, 99%), dimethylamine hydrochloride (97%), diethyl amine (98%), methanol (99.9+%), ethanol (anhydrous), and 2-chloroethylamine hydrochloride (98%), were all purchased from Aldrich Chemical Co. The ammonia (anhydrous) and monomethylamine (gas) were from Matheson.

3-Benzyloxypropionaldehyde (10-D) synthesis. 2.85 g of sodium hydroxide and 6.72 g of monochloroacetic acid were dissolved in water separately and then mixed. The solution was then mixed with 123 ml of benzyl alcohol and added to 100ml of acrolein in a 500ml flask dropwise. 30 ml of acetic acid was added to the flask and heated 80 hours at 40° C. The reaction was washed with water three times and dried with sodium sulfate. The product was obtained by distilling off the low boiling point fractions below 110° C. at reduced pressure (0.3 mmHg), 61 g, (31% yield) of 3-benzyloxypropionaldehyde (10-D) were obtained. NMR ($CDCl_3$): 9.67 (t, 1H, CHO, $J_{HH}$=0.033 Hz), 7.20 (s, 5 H, $C_6H_5$), 4.43 (s,2 H, $C_6H_5CH_2$), 3.73 (t. 2 H, $OCH_2$, $J_{HH}$=3 Hz), 2.60 (t of d, 2 H, $CH_2CHO$, $J_{HH}$=3 Hz, $J_{OH}$−1 Hz).

3-Benzyloxypropylidene diacetate (11-D) synthesis. 40 ml of acetic anhydride, 30 ml of ethyl ether and 3 ml of boron trifluoride/diethyl etherate were added to a 500 ml flask and 40 ml of 3-benzyloxypropionaldehyde was added to the flask in 5 minutes and stirred for another 10 minutes. The reaction mixture was washed with 200 ml of 10% sodium acetate and dried over sodium sulfate. The 3-benzyloxypropylidene (11-D) was crystallized on standing at −13° C. and recrystallized with acetone and hexane as a colorless solid at 75% yield. NMR (CDCl13): 7.67 (s, 5 H, C6H5), 6.90 (T, 1 H, CH(OAc)2, $J_{HH}=3$ Hz), 4.47 (s, 2 H, C6H5CH2), 3.73 (t,2 H, OCH2, $J_{HH}=3$ Hz), 1.90-2.23 (m, 2 H, CH2CH), 2.00 (S, 6 H, CH3). Anal. Calcd. for C14H18O5. C, 63.14; H, 6.81. Found: C, 63.44; H, 6.77.

3-Hydroxypropylidene diacetate (12-D) synthesis. 1 ml of 3-benzyloxypropylidene diacetate (11-D), 10 ml of ethylacetate, 0.1 g of 5% palladium-on-charcoal and 1 drop of perchloric acid were hydrogenolized at a pressure of 44 lb/inch$^2$ for 15 minutes. 0.5 g of calcium carbonate was shaken with the reaction mixture which was later filtered and then the solvent evaporated. The product (12-D) was obtained as a colorless oil which was quantitatively crystallized on standing at −13° C. NMR (CDCl3): 6.84 (t, 1 H, CH(OAc , $J_{HH}=3$ Hz), 4.91 (s, 1 h, HO), 3.67 (t, 2 H, HOCH2m $J_{HH}-3$ Hz), 2.16-1.83 (m, 2 H, CH2CH), 2.06 (M, 6 H, CH3). anal. Calcd. for C7H12O5. C, 47.72; H, 6.87. Found: C, 48.69; H, 6.80.

O (3,3-Diacetatopropyl)-N,N-bis(2-chloroethyl) phosphoramidic chloride (14-D) synthesis. A mixture of 2 ml of compound 12-D and 2 ml of triethylamine was added dropwise to 1.32 ml of phosphorous oxychloride in 20 ml of dichloromethane at −20° C., and the mixture was stirred for 20 minutes and then stirred at room temperature for 1 hour and 40 minutes more. 2.516 g of bis(2-chloroethyl) amine hydrochloride was added to the mixture, and then 4 ml of triethylamine was added dropwise at −20° C. and stirred for 20 minutes. The mixture was continuously stirred for 1 hour and 40 minutes at room temperature. The reaction mixture was twice washed with water, once with phosphate buffer (pH, 7.0) and twice with water, and then dried over sodium sulfate. After removing the solvent, the product (14-D) was purified by column chromatography (ethylacetate:hexane −1:1). 1.615 g of slightly yellow oil product was obtained, 29%. NMR (CDCl3): 6.83 (t, 1 H, CH(OAc), JHH=3 Hz), 4.43-4.00 (q, 2 H, OCH2, JHH=3 Hz, JOH=2.98 Hz), 3.77 (m, B H, CH2CH2Cl), 2.37-1.97 (m, 2 H, CH2CH), 2.07 (S, 6 H, CH3).

O-(3,3-Diacetatopropyl)-N,N-bis(2-chloroethyl) phosphorodiamide (15-D) synthesis. To 2.32 g of compound 14 was added 50 ml of 1 N ammonis in dichloromethane at −20° C. and the mixture was then stirred for 1 hour at room temperature. After the solvent was removed by evaporation, ether was added and the suspension was filtered. Ether was removed, and the residue was submitted to SiO2 column chromatography and eluted with chloroform and acetone (1:1) to give 1.57 g of product 15, (71%), as a yellow oil which was crystalized on standing at −13° C. NMR (CDCl3): 6.88 (t, 1 H, CH(OAc)2, JHH=3 Hz), 4.10 (q, 2 H, CH2O, JHH=3Hz, JHH−3 Hz), 3.3-3.8 (m, 10 H, CH2CH2Cl and NH), 2.0-2.3 (m, 2 H, CH2CH(OAc)2), 2.10 (s, 6H, CH3) Anal. Calcd. for C11H21Cl2N2O6P: C, 34.84; H, 5.58; N, 7.39. Found: C, 34.66; H, 5.44; N, 7.12.

O (3,3-Diacetatopropyl)-N,N-bis(2-chloroethyl)-N$^1$-methylphosphorodiamide (16-D) synthesis. 3.5 ml of 3 N monomethylamine in dichloromethane at −20° C. was added to 2.12 g of compound 14-D and stirred for 1 hour at room temperature. The other steps were the same as in making compound 15-D. 0.41 g of product (16-D) was obtained (20%) as a yellow oil. NMR (CDCl13): 6.86 (t, 1 H, CH(OAc2, JHH=3), 4.23-3.96 (Q, 2 H, OCH2, JHH=3 Hz, JOH−3 Hz), 3.76-3.15 (m, 8 H, CH2CH2Cl), 2.78-2.43 (m, 4 H, CH3NH), 2.18-1.95 (M, 2 H, CH2CH(OAc)2), 2.08 (s, 6 H, CH3). Anal. Calcd. for C12H23Cl2N2O6P: C, 36.65; H, 5.90; N, 7.13. Found: C, 36.59; H, 605; N, 7.30.

O (3,3-Diacetatopropyl)-N,N-bis(2-chloroethyl)-N$^1$-ethylphosphorodiamide (17-D) synthesis. To 2.055 g of compound 14-D in 20 ml of dichloromethane, 0.66 ml of ethylamine was added dropwise at −20° C., and the mixture was stirred for 75 minutes at room temperature. The other steps were the same as for making compound 15-D. 0.97 g of product (17-D) was obtained (46%) as a yellow oil. NMR (CDCl3): 6.83 (t, 1 H, CH(OAc)2, JHH=3 Hz), 4.19-3.86 (q, 2 H OCH2, JHH=3 Hz, JHH=3 Hz), 3.76-2.70 (m, 11 H, CH2CH2Cl and CH2NH, 2.26-1.93 (m, 2 H, CH2CH(OAc)2, 2.10 (s, 6 H, CH3), 1.26-0.98 (m, 3 H, CH3CH2NH). Anal. Calcd. for C13H25Cl2N2O6P: C, 38.34; H, 6.19; N, 6.88. Found: C, 38.25; H, 6.20; N, 6.63.

O-(3,3-Diacetatopropyl)-N,N-bis(2-chloroethyl)-N$^1$,N$^1$-dimethylphosphorodiamide (18-D) synthesis. To a mixture of 1.066 g of compound 14-D and 0.27 g of dimethylamine hydrocholride, 0.45 ml of triethylamine was added dropwise at −20° C. This was then stirred for 2 hours at room temperature. The other steps were the same as in making compound 15-D. 0.42 g of product was obtained as a yellow oil which was crystallized on standing at −13° C., 38%. NMR (CDCl3): 6.80 (t, 1 H, CH(OAc)2, JHH=3 Hz), 4.19-3.86 (q, 2 H, OCH2, JHH=3 Hz, JOH=3 Hz), 3.70-3.06 (m, 8 H, CH2CH2Cl), 2.73-2.56 (d, 6 H, (CH3)2N, JNH=% Hz), 2.26-1.96 (m,2 H, CH2CH(OAc)2), 2.05 (s, 6 H, CH3). Anal. Calcd. for C13H25Cl2N2O6P: C, 38.34; H, 6.19; N, 6.88. Found C, 37.91; H, 5.92; N, 6.47.

O (3,3-Diacetatopropyl)-N,N-bis(2-chloroethyl)-N$^1$,N$^1$-diethylphosphorodiamide (19-D) synthesis. To 6.04 g of compound 14-D in lo ml of dichloromethane, was added 0.31 ml of diethylamine dropwise at −20° C. The mixture was stirred for 3 hours at room temperature. The other steps were the same as in making compound 15-D. 0.239 g of product (19-D) was obtained as a yellow oil, 36%. NMR (CDCl3): 6.86 (t, 1 H, CH(OAc)2, JHH=3 Hz), 4.20-3.86 (q, 2 H, OCH2, JHH=3 Hz, JOH−3Hz), 3.76-280 (m, 12 H, CH2CH2Cl and CH3CH2N, 2.29-1.98 (m, 2 H, CH2CH(OAc)2, 2.03 (s, 6 H, CH3), 1.50 (t, 6 H, CH3CH2, JHH=3). Anal. Calcd. for C15H29Cl2N2O6P: C,41.39; H, 6.72; N, 6.44. Found: C, 41.59; H, 6.62; N, 6.24.

EXAMPLE 2

FURTHER SYNTHESIS OF CYCLOPHOSPHAMIDE ANALOGS

Alterations of the reaction conditions shown in Example 1 were performed as follows to synthesize other analogs. See FIG. 4.

Figure 4:
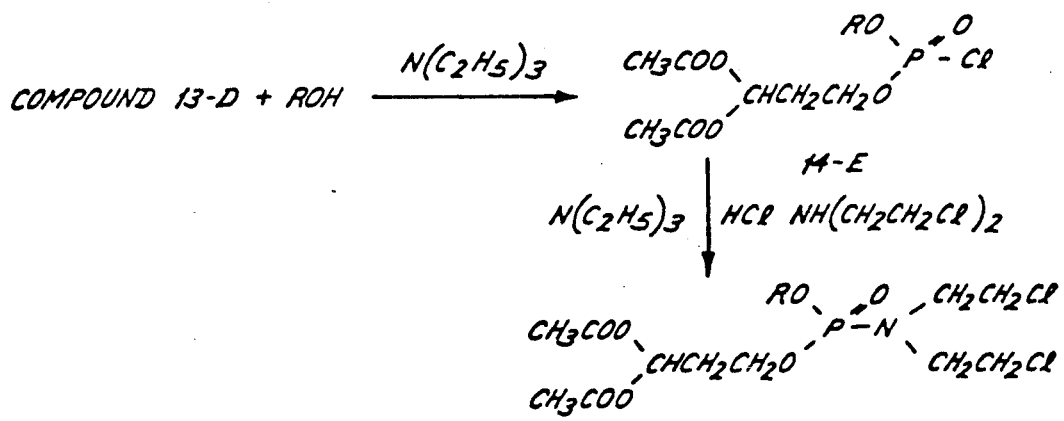
FIG. 4 further schematically shows a synthetic pathway for compounds of the present invention.

For the compounds 20-E and 21-E, the reaction sequence was altered. One equivalent of compound 12-D and triethylamine were added to 3 equivalents of phosphorus oxychloride. Instead of adding bis(2-chlrethyl)amine which would have produced compound (14-D), alcohol (ROH) (methanol or ethanol) and triethylamine were added to compound 13-D to produce compound 14-E. Then bis(2-chloroethyl)amine and triethylamine were added and compounds 20-E and 21-E were obtained by column chromatography (FIG. 4).

O (3,3-Diacetatopropyl)-O-methyl-N,N-bis(2-chloroethyl) phosphoramide (20-E) synthesis. To 0.33 ml of oxyphosphorous chloride in 10 ml of dichloromethane, a mixture of 0.5 ml of 12 and 0.5 ml of triethylamine at −20° C. was added dropwise, and stirred for 20 minutes and then for another 100 minutes at room temperature. A mixture of 0.2 ml of methanol and 0.5 ml of triethylamine was then added at −20° C., and stirred for 20 minutes and then for another 100 minutes at room temperature. 0.5 g of bis(2-chloroethyl)amine hydrochloride and 1 ml of triethylamine were added, again at −20° C., and stirred for 2 hours at room temperature. The other steps were as described in making compound 15-D. 0.189 g of product (20-E) was obtained as a yellow oil, 14%. NMR (CDCl$_3$), 6.86 (t, 1 H, CH(OAc)$_2$, JHH=3 Hz), 4.37-3.30 (m, 13 H, OCH$_2$, CH$_3$O and CH$_2$CH$_2$Cl), 2.26-2.06 (m, 2 H, CH$_2$CH(OAc)2, 2.03 (s, 6 H, CH$_3$). Anal. Calcd. for C$_{12}$H$_{22}$C$_{12}$N$_2$O$_7$P: C, 36.56; H, 5.63; N, 3.55. Found: C, 38.12; H, 5.92; N, 3.01.

O (3,3-Diacetatopropyl)-O-ethyl-N,N-bis(2-chloroethyl)phosphoramide (21-E) synthesis. The steps and reagents were the same with synthesizing compound 20-E except 0.27 ml of ethanol instead of methanol was used. 0.692 g of product (21-E) was obtained as a yellow oil, 48%. NMR (CDCl$_3$) 6.84 (t, 1 H, CH(OAc)$_2$, JHH=3 Hz),4.43-3.26 (m, 13 H, OCH$_2$, CH$_3$CH$_2$ and CH$_2$CH$_2$Cl, 2.23-2.03 (m, 2 H, CH$_2$CH(OAc)$_2$), 2.06 (s, 6 H, CH$_3$) 1.36 (t, 3 H, CH$_3$CH$_2$, JHH=3 Hz). Anal. Calcd. for C$_{13}$H$_{24}$Cl$_2$N$_2$O$_7$P: C, 38.25; H, 5.93; N, 3.43. Found: C, 38.01; H, 6.10; N, 3.16.

EXAMPLE 3

FURTHER CYCLOPHOSPHAMIDE ANALOG SYNTHESIS

Figure 5:
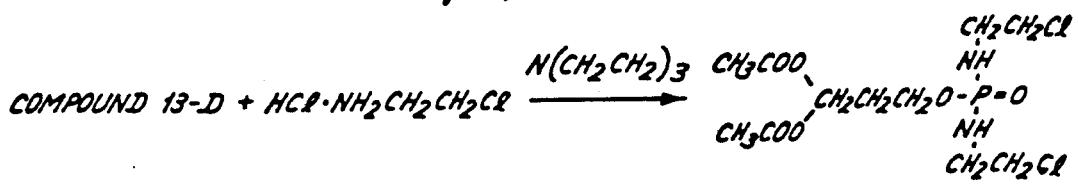
FIG. 5 schematically shows a synthetic scheme resulting in a compound of the present invention.

The modification as illustrated in FIG. 5 was used to produce compound 22-F.

O-(3,3-Diacetatopropyl)-N-(2-chloroethyl)-N-(2-chloroethyl)phosphorodiamide (22-F) synthesis. To 0.66 ml of oxyphosphorous chloride in 20 ml of dichloromethane was added a mixture of 1 ml of compound 12-D and 1 ml of triethylamine at −20° C. dropwise and stirred for 20 minutes, and the mixture was then stirred for another 100 minutes at room temperature. The other steps were as described in making compound 15-D (see FIG. 5). 0.32 g of product (22-F) was obtained as a yellow oil, 12% yield. NMR (CDCl$_3$) 6.89 (t, 1 H, CH(OAc)$_2$, JHH=3 Hz), 4.20-3.90 (q, 2 H, CH$_2$, JHH=3 Hz, JOH=3 Hz), 3.67-3.03 (m, 10 H, NH,NH and CH$_2$CH$_2$Cl), 2.26-2.00 (m, 2 H, CH$_2$CH(OAc)2). 2.06 (s, 6 H, CH$_3$). Anal. Calcd. for C$_{11}$H$_{21}$C$_{12}$N$_2$O$_6$P: C, 34.84; H, 5.58; N, 7.37. Found C, 35.30; H, 5.88; N, 6.57.

Cyclohexylammonium Hydrogen N,N-di-(2-chloroethyl)phosphorodiamidate synthesis. 25 g of bis(2-chloroethyl)amine hydrochloride in 65 ml of oxyphosphorus chloride was heated to reflux for 12 hours. The excess oxyphosphorus was removed by evaporation. Di(2-chloroethyl)phosphoramidic dichloride was crystallized from petroleum ether and acetone (1:1). It was recrystallized 3 times with the same solvent. 14.5 g of white crystals were obtained, m.p. 54°-56° C. This melting point was the same as that previously reported. 3 g of di(2-chloroethyl)phosphoramidic dichloride and 1.15 g of phenol were added to 20 ml of toluene and heated to reflux, 1.85 ml of triethylamine was then added over 2 minutes, the reflux continued for 4 hours and then left overnight. The suspension was filtered and the filtrate was submitted to SiO$_2$ column chromatography (hexane:ethylacetate=7:3). Phenyl-di(2-chloroethyl)phosphoramidic chloride was obtained as a yellow oil, 3.361 g, 92% NMR (CDCl$_3$): 7.3 (s, 5 H, C$_6$H$_5$), 3.87-3.33 (m, 8 H, CH$_2$CH$_2$Cl). 2.115 g of Phenyldi(2-chloroethyl) phosphoramidic chloride in toluene was bubbled with ammonia for 30 minutes. The precipitate was filtered and the solvent was removed by evaporation. The residue was diluted to cloudiness with petroleum ether and left overnight. Phenyl N,N-di(2-chloroethyl)phosphorodiamidate was crystallized, filtered, and without further purification, it was added to 50 ml of 100% ethanol and 0.4 g of platinum(IV) oxide and hydrogenolized for 15 minutes under the pressure 11 lb/inch$^2$. The mixture was filtered and 0.5 ml of cyclohexamine was added immediately. After the evaporation, the residue was washed onto a filter with ether. 0.501 g cyclohexylammonium hydrogen N,N-di(2-chloroethyl)phosphorodiamidate as an off-white powder was obtained, 23%, m.p. 124°-126° C.

EXAMPLE 4

ADDITIONAL CYCLOPHOSPHAMIDE ANALOG SYNTHESIS

Compounds B-8 to B-53 described in Table 1 were prepared by reaction of a precursor phosphoramidochloridate (compare FIG. 3, 14-D) or phosphorochloridate (compare FIG. 4 or FIG. 5) with the appropriate amine or alcohol by the methods described in Examples 1-3. Thus, compounds B-18 to B-25 and B-39 to B-53 were prepared by the methods described previously for compounds B-1 to B-7. The oxygen analogs B-26 to B-31 were prepared by the general procedure described for compounds B-8 and B-9. The phosphonate analogues B-33 to B-38 were prepared by the general method described below in Example 5.

EXAMPLE 5

Synthesis of: )-(3,3-Diacetoxypropyl)-N,N-bis(2-chloroethyl)methylphosphonamidochloridate (B-10). A solution of 3-hydroxypropionaldehyde diacetoxy acetal (12-D) (0.5 g, 2.8 mmoles) in CH$_2$Cl$_2$ (5 mL) was added simultaneously with a solution of Et$_3$N (0.4 ml, 2.8 mmoles) in CH$_2$Cl$_2$ (3 mL), over a period of 30 min, to a stirred solution of methylphosphonic dichloride (378 mg, 2.8 mmoles) in CH$_2$Cl$_2$ (5 mL) maintained at −30° C. in a dry-ice/acetone cooling bath. After 30 min. the reaction mixture was warmed to room temperature and stirred for 2 h. It was then cooled again to −30° C. and N,N-bis(2-chloroethyl)amine hydrochloride (0.5 g, 2.8 mmoles) was added followed by Et$_3$N (0.8 ml, 5.6 mmoles). After 30 min the reaction warmed to room temperature and stirred for a further 2 h. It was then washed with 0.45 M potassium phosphate buffer, pH 7.0 (20 mL) and H$_2$O (20 mL×2). The organic phase was dried over anhydrous Na$_2$SO$_4$. The solvent was evaporated and the remaining residue was submitted to flash chromatography on a column of silica using EtOAc-hexane (1:1, v/v) as eluent. Fractions (5 mL each) containing pure B-10 as evidenced by TLC analyses where combined and evaporated to give a viscous, pale yellow oil. It was dried in vacuo at 0.01 mm Hg over P$_2$O$_5$ for 48 h. Yield 456 mg (40%). $^1$H NMR (CDCl$_3$): 6.92 (t, 1 H, CH(OAc)$_2$), 3.90-4.32 (m, 2 H POCH$_2$), 3.60-3.67(t, 4 H, 2×CH$_2$Cl), 3.34-3.40 (m, 4 H, 2×NCH$_2$), 2.02-2.10 (m, 2 H, CHCH$_2$CH$_2$O), 2.05 (s, 6 H, 2×O-COCH$_3$), 1.28 (d, J=16 Hz, 3 H, CH$_3$).

EXAMPLE 6

IN VITRO CYTOTOXICITY OF COMPOUNDS SYNTHESIZED IN EXAMPLES 1-3

Certain of the above referenced compounds were tested against L1210 lymphatic leukemia cells in vitro, the results being shown in Table 2. Cyclophosphamide (CF), ASTA Z 7557 and phosphoramide mustard (PM) were used as positive controls. The toxicity of compounds 16-D to 19-D to L1210 cells were about the same. This suggested that the cyclic intermediate structure may not be essential for the antitumor selectivity because compounds 16-D and 17-D can cyclize, at least theoretically, but 18-D and 19-D cannot, due to their chemical structure. That compounds 15-D to 19-D and 22 were more effective than compounds 20-E and 21-E suggested that with a compound of the structure:

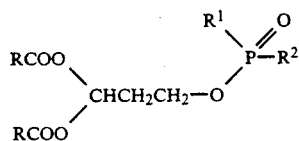

that $R^1$ being bound to the P through an N was important for antitumor activity. All of the 8 compounds were at least as toxic as ASTA Z 7557 and more toxic than phosphoroamide mustard, indicating that the aldehyde intermediate may be important for the antitumor selectivity. Compounds 15-D and 22-F, the precursor of the two clinically important antitumor drugs, cyclophosphamide and isophosphamide, respectively were much more toxic than ASTA Z 7557.

EXAMPLE 7

ACETALDOPHOSPHAMIDE: A PROMISING NEW ALTERNATIVE TO 4-HYDROPEROXYCYCLOPHOSPHAMIDE FOR THE IN VITRO ELIMINATION OF LEUKEMIC CELLS FROM HUMAN BONE MARRROW

In vitro active cyclophosphamide derivatives such as 4-hydroperoxycyclophosphamide (4-HC) have been widely investigated for their potential to eliminate malignant cells from bone marrow prior to hematopoietic rescue following intensive chemotherapy. Studies of the present invention suggest that 4-HC is more active against human (myelogenous) leukemia cells than against normal granulocyte-macrophage progenitors (GM-CFC). Using long-term human marrow cultures, a sparing effect of 4-HC on GM-CFC ancestor cells was also observed. These differential drug sensitivities may be due to different intracellular levels of aldehyde dehydrogenase, a key enzyme in the deactivation of aldophosphamide (ALD); the latter is an important intermediate in the conversion of 4-HC to the presumed ultimate active metabolite, phosphorodiamidic mustard. In a search for new stable precursors to an acetaldophosphamide (compound B-1, Table 1) was developed. The cytotoxic effects of compound B-1 on human normal GM-CFC and leukemia colony forming cells (L-CFC) were determined in vitro using both prolonged (8 days) and short-term (0.5–4.0 hr) drug exposures (see Table 3). Compound B-1 was approximately 10-fold more cytotoxic than 4-HC on a molar basis. The $IC_{50}$ values (the drug concentrations required to reduce colony formation to 50% of controls) of compound B-1 for normal human GM-CFC were approximately 2-fold

TABLE 2

| | Compound No. | | | | | | | | | |
|---|---|---|---|---|---|---|---|---|---|---|
| | 15-D | 16-D | 17-D | 18-D | 19-D | 20-E | 21-E | 22-F | CP | ASTA | PM |
| $ED_{50}$ (microgram/ml) | 0.6 | 5.8 | 6.4 | 7.1 | 7.8 | 13.0 | 13.6 | 1.7 | >20 | 13.0 | 18.0 |

$ED_{50}$ was the concentration of drug that kills 50% of the cells. The compounds were incubated with L1210 lymphotic leukemia cells for 72 hr at 37° C. with the compound over the concentration range 0.5-20 microgram/ml. The viability of the cells was determined by a spectrophotometric assay.

Drugs were dissolved in sterile water and filtered through a 0.22 um (micrometer) filter (Millipore Corporation). The stock drug solutions were 1 mg/ml. $2.5 \times 10^{-6}$ L1210 leukemia cells in 150 ul (microliter) RPMI 1640 medium complemented with 10% fetal calf serum were placed into every well of a 96 well plate. Drugs in 15 ul solution were then added and the cells were incubated for 72 hours at 37° C. $5 \times 10^{-4}$ mg of MTT in 15 ul solution was added to each well and then incubated for 4 hours at 37° C. Acid-isopropanol (180 ul of 0.04 N HCl in isopropanol) was added to each well to dissolve the crystallized dye produced The plates were read on a multiwell scanning spectrophotometer (ELISA reader) a wavelength of 570 nm. The ED50 values were calculated.

greater than those for the human myeloid cell line KBM-3 when assessed by continuous exposure. Interestingly, the $IC_{50}$ values for the GM-CFC after 1 hr drug exposure were 10-fold greater than those for the L-CF. Thus, compound B-1 is more cytotoxic to KBM-3 leukemic clonogeneic cells than to normal GM-CFC cells and the differential appears most pronounced after short-term exposure to relatively high drug concentrations.

TABLE 3

| | $IC_{50}$ (ng/mL; range) | |
|---|---|---|
| Cell type | 1 hr exposure | 8 days exposure |
| Normal, GM-CFC | 1,000–1,500 | 45–55 |
| KBM-3, L-CFC | 100–200 | 20–25 |
| Ratio GM-CFC/L-CFC | 10 | 2 |

Experiments further delineating the differential cytotoxicities of compound B-1 in comparison to 4-HC and in combination with other drugs are in progress are further confirming that compound B-1 is a promising new agent for the in vitro elimination of leukemic cells from bone marrow prior to autologous transplantation.

EXAMPLE 8

CYTOTOXIC GLYCOSIDE DERIVATIVES

Figure 6:
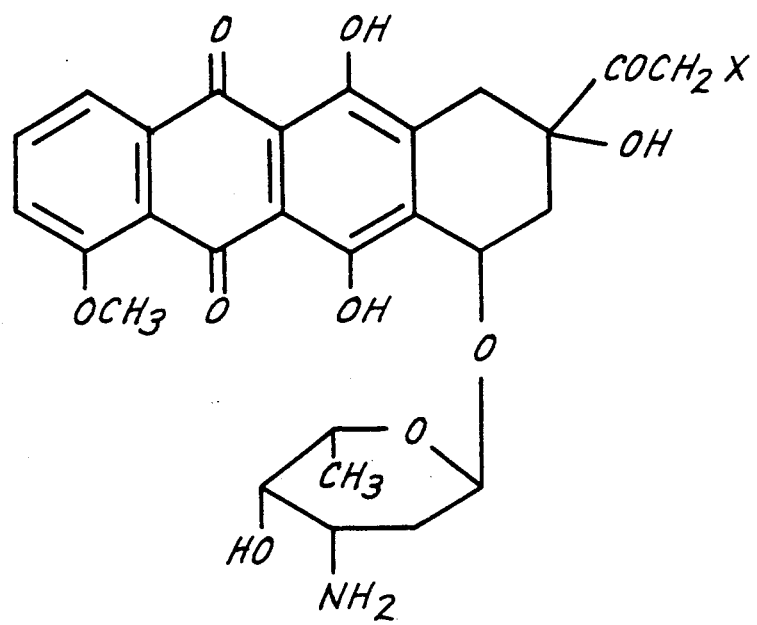
FIG. 6 schematically shows the structures of doxorubicin and daunomycin.

The cytotoxic glycoside antibiotics doxorubicin and daunomycin have the structures shown in FIG. 6. A number of bis(acyloxypropyl)phosphoramidates of the following general structure (C), where the $R^1$ group is doxorubicin or daunomycin bonded to the phosphorus through the sugar amino group, have been prepared.

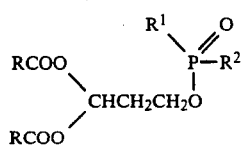
C

Table 4 shows the R, $R^1$ and $R^2$ substituents in structure C to produce compound No. C-1 to C-8.

TABLE 4

| Compound No. | R | $R^1$ | $R^2$ |
|---|---|---|---|
| C-1 | $CH_3$ | N-(3')-Doxorubicin | $N(CH_2CH_2Cl)_2$ |
| C-2 | $CH_3$ | N-(3')-Daunomycin | $N(CH_2CH_2Cl)_2$ |
| C-3 | $CH_3$ | N-(3')-Doxorubicin | $NHCH_2CH_2Cl$ |
| C-4 | $CH_3$ | N-(3')-Daunomycin | $NHCH_2CH_2Cl$ |
| C-5 | $C(CH_3)_3$ | N-(3')-Doxorubicin | $N(CH_2CH_2Cl)_2$ |
| C-6 | $C(CH_3)_3$ | N-(3')-Daunomycin | $N(CH_2CH_2Cl)_2$ |
| C-7 | $C(CH_3)_3$ | N-(3')-Doxorubicin | $NHCH_2CH_2Cl$ |
| C-8 | $C(CH_3)_3$ | N-(3')-Daunomycin | $NHCH_2CH_2Cl$ |

The preparation method for these compounds is described with respect to the prototype, N-[0-(3,3-diacetoxypropyl)-N,N-bis(2-chloroethyl)phosphorodiamido]-doxorubicin (C-1).

N,N-Diisopropylamine (0.032 mL, 0.2 mmoles) was added, with stirring, to a solution of doxorubicin free base (100 mg, 0.18 mmoles) in anhydrous chloroform/methanol (20:1) (15 ml). The mixture was cooled to −40° C. and 0-(3,3-diacetoxypropyl)]-N,N-bis(2-chloroethyl)phosphoramidochloridate (90 mg, 0.2 mmoles) in anhydrous dichloromethane (2 ml) was added. The reaction mixture was stirred for 30 min at −40° C., then at room temperature for 16 h. The solution was washed sequentially with an equal volume of 0.05 M phosphate buffer (pH 7) and water, and dried over $MgSO_4$. The solvent was evaporated and the residue was chromatographed on a column of silica using $CHCl_3/MeOH$ (20:1 to 5:1) as eluent. The product was isolated as a red solid. Yield 3 mg (14%). NMR ($CDCl_3/CD_3OD$) 13.91 (s, 1 H, OH), 13.18 (s, 1 H, OH), 7.94 (d, J=5 Hz, H-3, 7.72 (m, 1 H, H-2), 7.38 (d, J=5 Hz, H-1), 6.93 (t, 1 H, $CH(OAc)_2$), 5.20 (d, J=18 Hz, NHP), 4.7 (s, 2 H, $CH_2OH$), 4.01 (s, 3 H, $OCH_3$), 3.2–3.70 (m, 8H, $2 \times CH_2CH_2Cl$), 2.01 (s, 6H, $2 \times$)Ac), 1.06 (d, J=4 Hz, 3H, $CH_3$).

The anticipated mechanism of activation of these compounds is shown in FIG. 7. As shown in Scheme 1, compound C is hydrolyzed to the aldehyde C-I by tissue carboxylate esterases. In normal cells, C-I is then oxidized by aldehyde dehydrogenase to the carboxylic acid, C-II, a chemically unreactive compound. However, in tumor cells, which are comparatively deficient in aldehyde dehydrogenase, C-1 undergoes an E-2 elimination reaction to give C-III. The latter compound, like phosphorodiamidic mustard, should be chemically reactive and form covalent adducts with target DNA.

Such differential metabolism should not only lead to higher levels of the cytotoxic moiety C-III in tumor cells compared to normal cells, but might overcome resistance to the parent anthracyclines (doxorubicin, daunomycin, etc.) arising from efficient cellular drug efflux (the multidrug resistance phenotype).

Growth inhibition of cultured L1210 leukemia cells was used as a measure of the relative cytotoxicities of the anthracycline derivatives of the present invention.

L1210 murine leukemia cells were maintained in vitro by serial culture in RMPI Medium 1640 containing 10% heat-inactivated fetal calf serum, L-glutamine (2 micro-M/ml), 2-mercaptoethanol (10 micro-M), penicillin (50 U/ml), streptomycin 50 micro-g/ml) at 37° C. in a humidified atmosphere of 5% $CO_2$ and 95% air. Cells in exponential growth at a density of $10^6$ cells/ml were exposed to varying drug concentrations for 1 h at 37° C. They were then harvested by centrifugation for 5 min at 1500 RPM, washed twice with ice-cold phosphate-buffered saline (2 ml), resuspended in drug-free medium at a concentration of $2 \times 10^5$/ml, and cultured for 72 h. Cell viability was determined by the MTT assay. (Mossman, T (1983). Rapid colorimetric assay for cellular growth and survival application to proliferation and cytotoxicity assays. J. Immunol. Meth. 65:55–63). The concentrations of drug inhibiting cell growth 50% $IC_{50}$) is shown in Table 5.

TABLE 5

GROWTH INHIBITION OF
L1210 LEUKEMIA CELLS IN VITRO
BY DOSORUBICIN AND DAUNOMYCIN ANALOGUES[a]

| Compound | $IC_{50}$[b], (micromolar) |
|---|---|
| C-1) | 0.016 |
| C-2) | 0.018 |
| C-3) | 0.021 |
| C-4) | 0.025 |
| C-5) | 0.017 |
| C-6) | 0.020 |
| C-7) | 0.035 |
| C-8) | 0.030 |

[a]Exponentially growing cells were exposed to varying drug concentrations for 96 h at 37° C. The cells were then centrifuged, resuspended, and cultured in drug-free medium for 72 h.
[b]The drug concentration that inhibited cell growth by 50% compared to untreated control cultures.

EXAMPLE 9

NUCLEOSIDE DERIVATIVES

Nucleoside analogues of the following general structure (D) were prepared as potential antitumor and anti-AIDS agents.

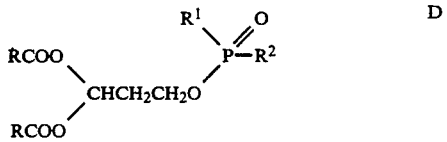
D

Table 6 shows the R, $R^1$ and $R^2$ substituents of structure D for compounds D-1 to D-4.

TABLE 6

NUCLEOSIDE DERIVATIVES SYNTHESIZED

| Compound No. | R | $R^1$ | $R^2$ |
|---|---|---|---|
| D-1 | $CH_3$ | $NH_2$ | 2',3'-dideoxyuridine-5'-yl |
| D-2 | $C(CH_3)_3$ | $NH_2$ | 2',3'-dideoxyuridine-5'-yl |
| D-3 | $CH_3$ | $NH_2$ | 5-methyl-2',3'-dideoxyuridine-5'-yl |
| D-4 | $C(CH_3)_3$ | $NH_2$ | 5-methyl-2',3'-dideoxyuridine-5'-yl |

The method of synthesis of these compounds can be illustrated with respect to the 2',3' dideoxyuridine derivative (D-1).

A solution of 1,2,4-triazole (132.23 mg, 1.92 mmole) and POCl$_3$ (98 mg, 60 ul, 0.639 mmoles) was dissolved in dioxane (2 mL) [dried over 4 Angstrom molecular sieves (300° C./1 h)] and a solution of triethylamine (267 uL, 1.92 mmole) in dioxane (1 mL) was added dropwise during a 45 min period. After stirring for an additional 40 min, the reaction mixture was filtered under nitrogen into a flask containing dideoxyuridine (90.4 mg; 0.426 mmoles) which has previously been evaporated with pyridine. After 30 min, a solution of 3-hydroxypropionaldehyde diacetoxy acetal (97.5 mg, 0.55 mmole) in dioxane (0.5 mL) was added. After stirring at room temperature for 5 hr the reaction mixture was concentrated to ⅓ of the starting volume and 1.3 mL of a 1.6 N solution of ammonia (2.13 mmole) in dioxane was added. After 30 min the reaction mixture was evaporated to dryness and the residue was taken up in the minimum volume of methanol and chromatographed on two thick layer (2 mm) plates (20×20) of silica. The product was isolated as a viscous colorless oil. Its NMR spectra was consistent with the assigned structure.

The effectiveness against growth of L1210 cells of these nucleoside analogs was tested and the growth inhibition shown in Table 7.

TABLE 7
GROWTH INHIBITION OF L1210 LEUKEMIA CELLS IN VITRO BY NUCLEOSIDE ANALOGUES[a]

| Compound | IC$_{50}$[b], micro-M |
| --- | --- |
| D-1) | 1.4 |
| D-2) | 0.7 |
| D-3) | 1.3 |
| D-4) | 1.6 |

[a]Exponentially growing cells were exposed to varying drug concentrations for 96 h at 37° C. The cells were then centrifuged, resuspended, and cultured in drug-free medium for 72 h.
[b]The drug concentration that inhibited cell growth by 50% compared to untreated control cultures.

EXAMPLE 10
PREDICTED MECHANISM OF ACTIVATION

The anticipated mechanism of activation of these compounds is shown in FIG. 8. Scheme 2 shows that compound G (where R$_1$ is a cytotoxic moiety) is converted to the aldehyde G-I by tissue esterases. In normal cells, G-I is preferentially converted to the carboxylic acid, G-II, by aldehyde dehydrogenase. G-II should be chemically stable and biologically inert. In tumor cells, however, G-I should undergo E-2 elimination to give the phosphorodiamidate, G-III. This compound will then be converted to the corresponding phosphate, G-IV, by spontaneous chemical or enzymatic hydrolysis. Such differential metabolism should lead to higher levels of the R$^1$ cytotoxin such as a cytotoxic mustard, adriamycin or nucleotide analogue, G-IV, in tumor cells.

x x x x x x x

Changes may be made in the construction, operation and arrangement of the various compounds and procedures described herein without departing from the concept and scope of the invention as defined in the following claims.

What is claimed is:

1. A compound having the structure

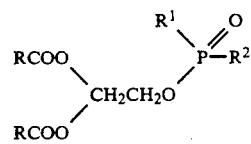

wherein
R is CH$_3$ [or C$_2$H$_5$];
R$^1$ is NHC$_3$H$_7$, NHC$_4$H$_9$, [NCH$_3$(C$_2$H$_5$), NCH$_3$(C$_3$H$_7$),] NHC$_6$H$_5$, [NHOH, NHNHCO$_2$CH$_2$C$_6$H$_5$, NHNHCO$_2$C(CH$_3$)$_2$,] OC$_3$H$_7$, OC$_4$H$_9$, OC$_6$H$_5$, or OCH$_2$C$_6$H$_5$, [ONHCO$_2$C(CH$_3$)$_3$, OCH$_2$CH$_2$CH(OAC)$_2$, OP(O)N(CH$_2$CH$_2$Cl)$_2$, C$_3$H$_7$, C$_4$H$_9$, CH$_2$NO$_2$ or CH$_2$NH$_2$]; and
R$^2$ is [NHCH$_2$CH$_2$Cl or] N(CH$_2$CH$_2$Cl)$_2$.

* * * * *

UNITED STATES PATENT AND TRADEMARK OFFICE
CERTIFICATE OF CORRECTION

PATENT NO. : 5,091,552
DATED : February 25, 1992
INVENTOR(S) : David Farquhar and Yugiang Wang It is certified that error appears in the above-indentified patent and that said Letters Patent is hereby corrected as shown below:

In claim 1, column 22, line 33 immediately in front of the term 'CH$_2$CH$_2$O' insert the term --CH--.

In claim 1, column 22, line 38 delete all bracketed material.

In claim 1, column 22, line 39-40 delete all bracketed material.

In claim 1, column 22, line 40-41 delete all bracketed material.

In claim 1, column 22, line 42-45 delete all bracketed material.

In claim 1, column 22, line 46 delete all bracketed material.

UNITED STATES PATENT AND TRADEMARK OFFICE
CERTIFICATE OF CORRECTION

PATENT NO. : 5,091,552
DATED : February 25, 1992
INVENTOR(S) : David Farquahar and Yugiang Wang It is certified that error appears in the above-indentified patent and that said Letters Patent is hereby corrected as shown below:

On the title page, Item [75]  insert the name of coinventor
--Yuqiang Wang--.

In column 5, line 5 immediately in front of the term '$CH_2CH_2O$' insert the term --CH--.

In column 5, line 9 insert --,-- immediately after the term '$CH_3$.

In column 6, line 6 immediately in front of the term '$CH_2CH_2O$' insert the term --CH--.

In column 6, line 49 immediately in front of the term '$CH_2CH_2O$' insert the term --CH--.

In column 7, line 6 immediately in front of the term '$CH_2CH_2O$' insert the term --CH--.

In column 7, line 23 immediately in front of the term '$CH_2CH_2O$' insert the term --CH--.

Signed and Sealed this

Fifth Day of October, 1993

*Attest:*

BRUCE LEHMAN

*Attesting Officer*  *Commissioner of Patents and Trademarks*